United States Patent
Zigel et al.

(10) Patent No.: US 11,633,150 B2
(45) Date of Patent: Apr. 25, 2023

(54) APPARATUS AND METHOD FOR DIAGNOSING SLEEP QUALITY

(71) Applicants: BEN GURION UNIVERSITY OF THE NEGEV RESEARCH AND DEVELOPMENT AUTHORITY, Beersheva (IL); MOR RESEARCH APPLICATIONS LTD, Tel Aviv (IL)

(72) Inventors: Yaniv Zigel, Omer (IL); Eliran Dafna, Beersheva (IL); Ariel Tarasiuk, Meitar (IL)

(73) Assignees: BEN GURION UNIVERSITY OF THE NEGEV RESEARCH AND DEVELOPMENT AUTHORITY, Beersheva (IL); MOR RESEARCH APPLICATIONS LTD., Tel Aviv (IL)

(*) Notice: Subject to any disclaimer, the term of this patent is extended or adjusted under 35 U.S.C. 154(b) by 980 days.

(21) Appl. No.: 14/404,621

(22) PCT Filed: May 30, 2013

(86) PCT No.: PCT/IB2013/054469
§ 371 (c)(1),
(2) Date: Nov. 30, 2014

(87) PCT Pub. No.: WO2013/179254
PCT Pub. Date: Dec. 5, 2013

(65) Prior Publication Data
US 2015/0119741 A1  Apr. 30, 2015

Related U.S. Application Data

(60) Provisional application No. 61/653,426, filed on May 31, 2012.

(51) Int. Cl.
*A61B 5/00* (2006.01)
*A61B 7/00* (2006.01)
(Continued)

(52) U.S. Cl.
CPC .......... *A61B 5/4812* (2013.01); *A61B 5/0816* (2013.01); *A61B 5/4809* (2013.01);
(Continued)

(58) Field of Classification Search
CPC ................ A61B 5/4812; A61B 5/4815; A61B 5/7264; A61B 7/003
See application file for complete search history.

(56) References Cited

U.S. PATENT DOCUMENTS

2004/0193068 A1* 9/2004 Burton ................ A61B 5/4812
                                                              600/544
2004/0230105 A1  11/2004 Geva
(Continued)

OTHER PUBLICATIONS

International Search Report dated Nov. 1, 2013 for corresponding PCT application PCT/IB2013/054469, international filing date May 30, 2013.
(Continued)

*Primary Examiner* — Christian Jang
*Assistant Examiner* — Karen E Toth
(74) *Attorney, Agent, or Firm* — Nixon & Vanderhye PC

(57) ABSTRACT

A method of distinguishing sleep period states that a person experiences during a sleep period, the method comprising: using a non-contact microphone to acquire a sleep sound signal representing sounds made by a person during sleep; segmenting the sleep sound signals into epochs; generating a sleep sound feature vector for each epoch; providing a first model that gives a probability that a given sleep period state experienced by the person in a given epoch exhibits a given sleep sound feature vector; providing a second model that gives a probability that a first sleep period state associated with a first epoch transitions to a second sleep period state associated with a subsequent second epoch; and processing the feature vectors using the first and second models to
(Continued)

determine a sleep period state of the person from a plurality of possible sleep period states for each of the epochs.

18 Claims, 5 Drawing Sheets

(51) Int. Cl.
*G16H 50/00* (2018.01)
*G16H 15/00* (2018.01)
*G16H 50/30* (2018.01)
*G16H 50/20* (2018.01)
*G16H 10/60* (2018.01)
*A61B 5/08* (2006.01)
*A61B 7/04* (2006.01)

(52) U.S. Cl.
CPC .......... *A61B 5/4815* (2013.01); *A61B 5/4818* (2013.01); *A61B 5/6898* (2013.01); *A61B 5/7264* (2013.01); *A61B 5/7275* (2013.01); *A61B 5/7278* (2013.01); *A61B 7/003* (2013.01); *A61B 7/04* (2013.01); *G16H 10/60* (2018.01); *G16H 15/00* (2018.01); *G16H 50/00* (2018.01); *G16H 50/20* (2018.01); *G16H 50/30* (2018.01); *A61B 5/0823* (2013.01); *A61B 5/0826* (2013.01)

(56) References Cited

U.S. PATENT DOCUMENTS

| | | | |
|---|---|---|---|
| 2007/0016095 A1 | 1/2007 | Low | |
| 2009/0234241 A1* | 9/2009 | Ota | A61B 7/003 |
| | | | 600/529 |
| 2010/0049008 A1 | 2/2010 | Doherty | |
| 2011/0034811 A1 | 2/2011 | Naujokat | |
| 2011/0295083 A1 | 12/2011 | Doelling | |
| 2012/0088992 A1* | 4/2012 | Armitstead | A61B 5/7267 |
| | | | 600/323 |
| 2012/0092171 A1 | 4/2012 | Hwang | |
| 2012/0190996 A1* | 7/2012 | Tanaka | A61B 7/003 |
| | | | 600/529 |
| 2013/0261485 A1* | 10/2013 | Ishikawa | A61B 7/003 |
| | | | 600/529 |
| 2013/0310657 A1* | 11/2013 | Sullivan | A61B 5/7405 |
| | | | 600/301 |
| 2020/0093423 A1* | 3/2020 | Dafna | A61B 5/1118 |

OTHER PUBLICATIONS

Scalart P, Filho JV (1996); "Speech Enhancement Based on A Priori Signal to Noise Estimation"; Conf Proc IEEE International Conference on Acoustics, Speech, and Signal Processing 2: 629-632.

* cited by examiner

APPARATUS AND METHOD FOR DIAGNOSING SLEEP QUALITY

RELATED APPLICATIONS

The present application is a U.S. National Phase of PCT Application PCT/IB2013/054469, filed on May 30, 2013, which claims the benefit under 35 U.S.C. 119(e) of U.S. Provisional Application 61/653,426 filed on May 31, 2012, the disclosure of which is incorporated herein by reference.

TECHNICAL FIELD

Embodiments of the invention relate assessing sleep quality.

BACKGROUND

Sleep disorders appear to be quite widespread, and complaints and worries about real or imagined sleep disorders and levels of discomfort with respect to how much sleep one gets and quality of sleep are common subjects for discussion. It is estimated that between 40% and 60% of the population in modern societies are affected, or possibly believe they are affected to some degree by sleep disorder. Real sleep disorders can be serious and may be considered to be disease conditions on their own and/or can lead to disease conditions that interfere with normal physical, mental, and/or emotional functioning.

By way of example, it is estimated that 60% of the population suffer from insomnia, 30-70% suffer from snoring, and between 2% to 7% of the population suffer from obstructive sleep apnea (OSA). OSA is characterized by repetitive collapse or narrowing of the upper airway passages during sleep that impairs ventilation, may lead to total or near total cessation of breathing and disrupts sleep. OSA events are typically associated with episodes of snoring that may be followed by long silent periods during which there is no breathing. The periods of no breathing are typically followed by neurological arousal of the person from sleep that initiates activity to reopen the upper airway passages and reestablish breathing. The activity to reestablish breathing is generally accompanied by relatively intense, loud snorts and/or gasps as the person struggles to regain breathing.

Sleep disorders can result in a spectrum of undesirable effects that includes besides anxiety, daytime drowsiness, impairment of concentration and motor functions, and potentially relatively long term, serious health risks. For example, OSA is associated with increased cardiovascular morbidity.

Conventionally, diagnosing a person's sleep disorders, and in particular OSA, involves performing a sleep study, referred to as polysomnography, (PSG). PSG is a relatively complicated and expensive procedure that is carried out in a sleep laboratory during the person's overnight stay in the laboratory. PSG typically involves attaching a variety of sensors to the patient's body to track performance of a battery of physiological activities and functions. The tracked activities and functions may include brain activity, eye motion, skeletal muscle activation, respiratory efforts, and heart function during sleep.

In addition to being uncomfortable, expensive, and equipment intensive, PSG studies to determine quality and disturbances of a person's sleep are not readily accessible. It is estimated for example, that the waiting period for PSG has been reported to be a few weeks to more than a year in the United States.

SUMMARY

An aspect of an embodiment of the invention relates to providing a non-contact method for distinguishing a person's states of sleep from states of his or her wakefulness responsive to sounds that the person makes during a sleep period. A "sleep period" refers, by way of example, to a period, such as a nocturnal sleep period, a siesta period, or a period of dozing, during which a person exhibits a state of sleep, or exhibits states of sleep interrupted by a state of wakefulness. A state of wakefulness may be referred to as an "awake state". The sounds, hereinafter also referred to as "sleep sounds", that the person makes during the sleep period are acquired using a non-contact microphone, which generates sleep sound signals representative of the sleep sounds. The sleep sound signals are processed to determine whether sleep sounds made by the person during each of a sequence of consecutive time segments into which the sleep period may be segmented indicate that the person is in a sleep state or an awake state during the segment. According to an aspect of an embodiment of the invention, data characterizing the sleep and awake states determined for the time segments are processed to generate a set of sleep quality parameters (SQPs), which are used to provide measures of the sleep quality of the person during the sleep period. Sleep and awake states during a sleep period are generically referred to as "sleep period states"

In an embodiment of the invention, the sleep sound signals are processed to determine a set of features, "sleep sound features", of sleep sounds for each segment that may be used to indicate whether the person is in a sleep state or an awake state during the segment. A classifier uses the sleep sound feature vectors to determine whether sleeps sounds generated by the person during a segment of the sleep period indicate that the person is in a sleep state or an awake state during the segment. The set, also referred to as a sleep sound feature vector, of sleep sound features may comprise a respiratory rhythm period (RRP), a respiratory rhythm intensity (RRI), and a snore likelihood score (SLS), for the time segment.

In an embodiment of the invention, the classifier determines whether a given segment of the sleep period is associated with a sleep or awake state responsive to a probability that the sleep sound feature vector for a given segment is associated with a sleep or awake state, and a model that provides probabilities for transitions between sleep and awake states. Optionally, the probability relating a sleep sound feature vector to a sleep period state is provided by a probability function that comprises a Gaussian Mixture model (GMM) of the relationship between sleep sound feature vectors and sleep period states. The model providing transition probabilities may be a hidden Markov model (HMM) configured having a sleep state and an awake state. Optionally the HMM is a two state HMM. The GMM and HMM may be trained on a set of sleep period states determined to be sleep or awake states in accordance with a suitable gold standard procedure, such as a PSG study in a sleep laboratory involving human classification of sleep states.

In an embodiment of the invention, the set of SQPs comprise at least two or more, or any combination of two or more SQPs, such as total sleep time (TST) a sum of the durations of sleep states in a sleep period; sleep latency (SL)

an elapsed time to falling asleep from a time of lying down to go to sleep; sleep efficiency (SE) a ratio between TST and total time spent lying down to sleep during the sleep period; wake-time after sleep onset (WASO) a sum of the durations of awake states during the sleep period; and an awakening index (AI) equal to an average number of times per hour a person awakes from sleep during the sleep period.

An aspect of an embodiment of the invention relates to providing a method of distinguishing different sleep states responsive to sleep sound signals and using occurrence of different sleep states to provide a measure of quality of a person's sleep. Optionally, the different states of sleep comprise a state of rapid eye movement (REM) sleep and a state of non-REM (NREM) sleep. In an embodiment of the invention, a sleep sound feature vector comprises a feature or features that may be used to advantage in distinguishing REM from NREM sleep states. The feature or features may comprise at least one or more features that provides a measure of lability of activity of a person during a sleep period, such as a measure of respiration rate variability (RRV) or variability of time delay (VOD) between a breath inhale and a breath exhale.

In experiments performed to compare SQPs determined in accordance with an embodiment of the invention with SQPs determined using a conventional PSG method, measurements of SQPs were acquired for sleep periods for a group of people using both methods. Measurements for same SQPs determined by both methods were substantially the same to within standard deviations associated with the measurements.

There is therefore provided in accordance with an embodiment of the invention, a method of distinguishing sleep period states that a person experiences during a sleep period, the method comprising: using a non-contact microphone to acquire a sleep sound signal representing sounds made by a person during sleep; segmenting the sleep sound signals into epochs; generating a sleep sound feature vector for each epoch; providing a first model that gives a probability that a given sleep period state experienced by the person in a given epoch exhibits a given sleep sound feature vector; providing a second model that gives a probability that a first sleep period state associated with a first epoch transitions to a second sleep period state associated with a subsequent second epoch; and processing the feature vectors using the first and second models to determine a sleep period state of the person from a plurality of possible sleep period states for each of the epochs. Optionally, the first model comprises a Gaussian mixture model (GMM). Optionally, the second model comprises a hidden Markov model (HMM).

In an embodiment of the invention, processing the feature vectors using the first and second models to determine a sleep period state for each of the epochs comprises determining for each epoch a probability that the person is experience an awake state p(A) and a probability p(S) that the person is experiencing a sleep state during the epoch. Optionally, the method comprises determining a value for a classification metric, CM, for the epoch responsive to p(A) and p(S) for the epoch. The method may comprise determining that the person is experiencing an awake state or a sleep state during the epoch responsive to the value of the CM and a classifier threshold for the CM value.

In an embodiment of the invention, the method comprises using the determined sleep period states to determine a sleep quality parameter (SQP) indicative of a quality of sleep for the person. Optionally, using the sleep period states to determine a SQP comprises determining a value for at least one, or any combination of: a total sleep time (TST); sleep latency (SL); sleep efficiency (SE); wake-time after sleep onset (WASO); and/or an awakening index (AI).

In an embodiment of the invention, the sleep sound vector comprises a value for at least one of, or for each of any combination of: a respiratory rhythm period (RRP); a respiration rate intensity (RRI); a snore likelihood (SL); and/or at least one lability feature. Optionally determining a value for RRP comprises determining an autocorrelation function as a function of time displacement for sleep sounds that occurred during the epoch.

Determining a value for RRI may comprise determining a line tangent to a maximum of the autocorrelation for a time displacement equal to zero and a first maximum of the correlation function for a time displacement greater than zero. Optionally the method comprises, determining a value for an area factor responsive to an area between the tangent line and the autocorrelation function, and determining a value for RRI responsive to the area function and the magnitude of the first maximum.

In an embodiment of the invention, determining a snore likelihood comprises: identifying a portion of the sleep sound signal having an energy greater than a threshold energy and duration greater than a minimum duration; determining a snore feature vector for the portion; and determining a probability, p(snore), that the portion exhibits a snore and a probability, p(noise), that the portion exhibits noise rather than a snore responsive to the snore feature vector. Optionally, determining snore likelihood comprises determining the snore likelihoodSL equal to a snore likelihood score SLS that is a function of p(snore) and p(noise). Determining SLS optionally comprises determining an event score equal to (log p(snore)–log p(noise) for the portion. Optionally, determining SLS comprises determining SLS to be equal to a maximum of event scores for portions of the sleep sound signal in the epoch.

In an embodiment of the invention, a lability feature comprises least one of, or any combination of: a measure of respiration rate variability (RRV), variability of time delay (VOD) between a breath inhale and a breath exhale, variability in RRI, and/or snores duration.

There is further provided in accordance with an embodiment of the invention, apparatus for distinguishing sleep period states that a person experiences during a sleep period, the apparatus comprising: at least one non-contact microphone configured to acquire a sleep sound signal representing sounds made by a person during sleep; and a processor having an executable instruction set configured to: segment the sleep sound signals into epochs; generate a sleep sound feature vector for each epoch; and process the feature vectors using first and second models to determine a sleep period state of the person from a plurality of possible sleep period states for each of the epochs; wherein the first model gives a probability that a given sleep period state experienced by the person in a given epoch exhibits a given sleep sound feature vector and the second model gives a probability that a first sleep period state associated with a first epoch transitions to a second sleep period state associated with a subsequent second epoch.

Optionally, the at least one non-contact microphone comprises a plurality of non-contact microphones. In an embodiment of the invention, at least a portion of the apparatus is housed in a smartphone, PC, laptop, and/or a work book.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. A label labeling an icon representing a given feature of an embodiment of the invention in a figure may be used to reference the given feature. Dimensions of components and features shown in the figures are chosen for convenience and clarity of presentation and are not necessarily shown to scale.

DETAILED DESCRIPTION

Figure 1:
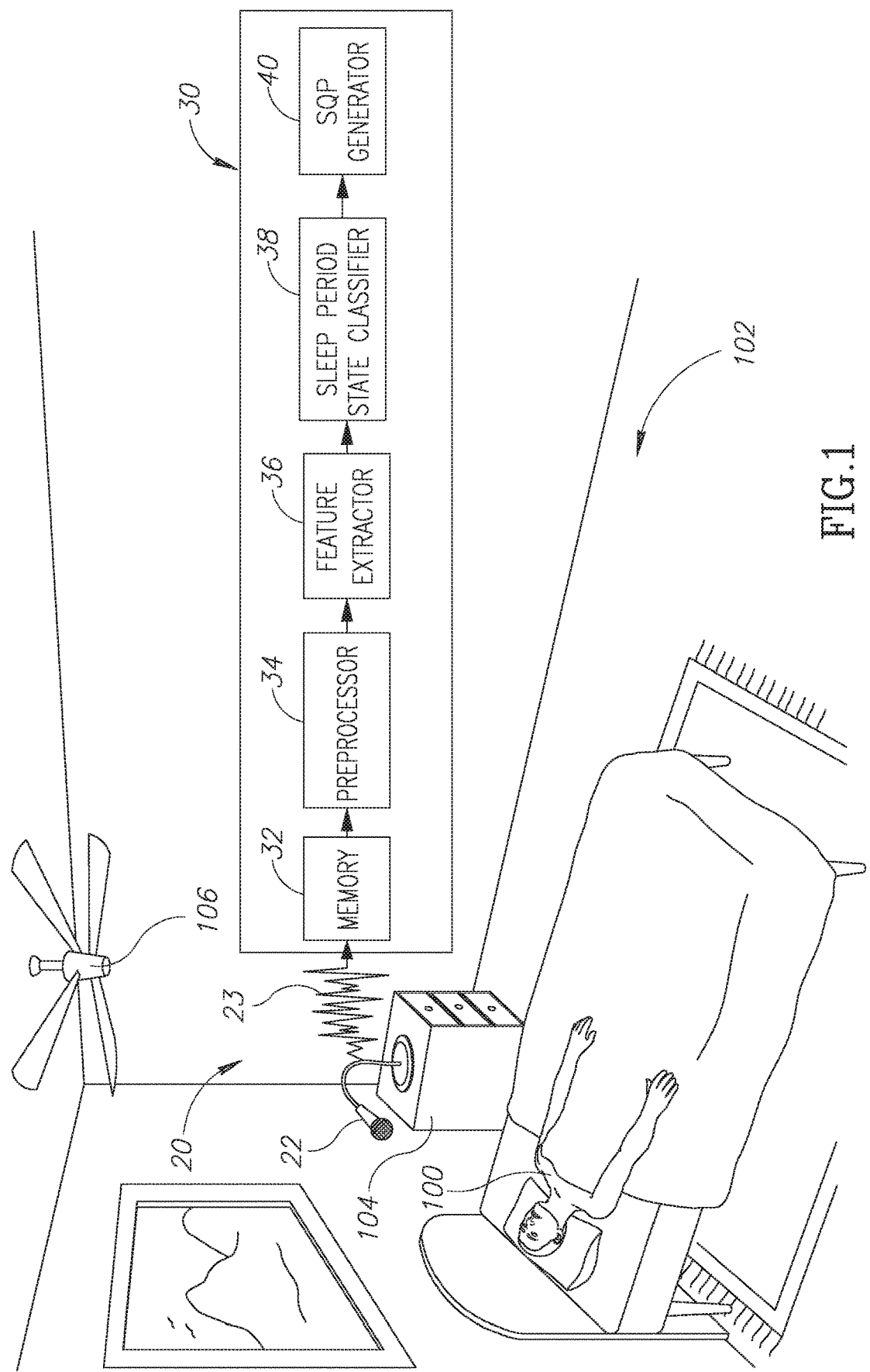
FIG. 1 schematically shows apparatus operating to distinguish sleep period states of a person optionally during a nighttime sleep period and generate SQPs for the person responsive to the person's sleep sounds, in accordance with an embodiment of the invention.

FIG. 1 schematically shows a non-contact sleep quality detection apparatus 20, referred to for convenience of presentation as "SleepDetective" 20, operating to generate SQPs for a sleeping person 100 in accordance with an embodiment of the invention. Person 100 is by way of example assumed to be sleeping at night in a bedroom 102 of his own house. SleepDetective 20 comprises a computer system 30 and at least one microphone, represented by a microphone 22, optionally placed on a night table 104 near person 100, and optionally directly connected to the computer system.

Microphone 22 registers sleep sounds made by person 100 during the person's nighttime sleep period sleep and sounds that are not made by the person that reach the microphone during the sleep period. Sounds that are made by the person comprise for example, breathing sounds, snoring sounds, coughing and voice sounds, and motion sounds that are produced by motion of the person, such as bed creaking and blanket rustling sounds. Sounds that are not made by the person may comprise street sounds and sounds originating in other rooms of the person's house that reach the bedroom, and sounds made by appliances, such as a whining sound made by an overhead fan 106 in bedroom 102. Sounds not made by the person may also include sounds made by another person (not shown) in the bedroom.

For convenience of presentation, sounds that are registered by microphone 22 that are not sleep sounds made by person 100 are referred to as background noise, or noise. Microphone 22 transmits the sounds that it registers as signals schematically represented by a waveform 23, also referred to as signal 23, optionally in real time directly to computer system 30 and/or to an interim memory for later transmittal to the computer system. Signal 23 generally comprises sleep sound signals mixed with varying amounts of noise signals, also referred to simply as noise, responsive to background noise.

Computer system 30 processes signal 23 using a method in accordance with an embodiment of the invention discussed below, to identify different sleep period states that person 100 exhibits during sleep and process characteristics of the sleep period states to provide a set of SQPs usable to indicate quality of sleep that person 100 experiences. Computer system 30 may comprise a memory 32 for storing signal 23 that it receives from microphone 22 and is optionally configured having a computer executable instruction set that may have a preprocessor 34, a feature extractor 36, a sleep period state classifier 38, and a SQP generator 40.

Preprocessor 34 processes signal 23 stored in memory 32 to increase signal to noise and reduce adulteration of sleep sounds such as snoring and breathing sounds, and optionally motion sounds, in signal 23 by noise. Feature extractor 36 processes preprocessed signal 23 in accordance with an embodiment of the invention to determine sleep sound features and generate sleep sound feature vectors that may be used to distinguish states of sleep from awake states during the nighttime sleep of person 100. In an embodiment of the invention, the sleep sound features are determined for and define a sleep sound feature vector for each of a series of sequential time segments of signal 23. The sleep sound feature vector for a given time segment may comprise measures of respiratory rhythm period (RRP), respiratory rhythm intensity (RRI), and snore likelihood score (SLS) determined for the segment.

Sleep period state classifier 38 operates on the sleep sound feature vectors determined for the segments to determine for each of the segments whether person 100 is in a sleep state or an awake state. Sleep period state classifier 38 is configured to make the determinations using models that provide transition probabilities between sleep and awake states and a probability that a given sleep sound feature vector is generated by a given sleep or awake state. In an embodiment of the invention, sleep period state classifier 38 is trained on a training set of sleep period time segments for which sleep period states are determined in accordance with a suitable gold standard procedure, such as a PSG study in a sleep laboratory involving human classification of sleep period states. SQP generator 40 processes data that characterizes the sleep period states determined for segments of the nighttime sleep period of person 100 to provide SQPs that may be used to provide an assessment of the sleep quality of the sleep period.

Computer system 30 may be comprised in or comprise any real or virtual computer system or communication device having access to suitable computer resources. For example, the computer system may comprise or be comprised in a smartphone, PC, a laptop, and/or a work book. Computer system 30 may be a distributed system having components and executable instruction sets located in different servers, and may be partially or completely based on access to servers via the internet, that is partially or completely "cloud based". For example, memory 32 may be located close to microphone 22 and directly coupled to the microphone by a wire or wireless communication channel to receive and store sleep sound signal 23. Preprocessor 34, feature extractor 36, sleep period state classifier 38, and SQP generator 40 may be connected to memory 32 and each other by the internet and reside and function in different internet servers. And whereas microphone 22 is shown separate from computer system 30 it may be comprised as a component in apparatus, for example a smartphone, housing at least a portion of computer system 30.

Figure 2:
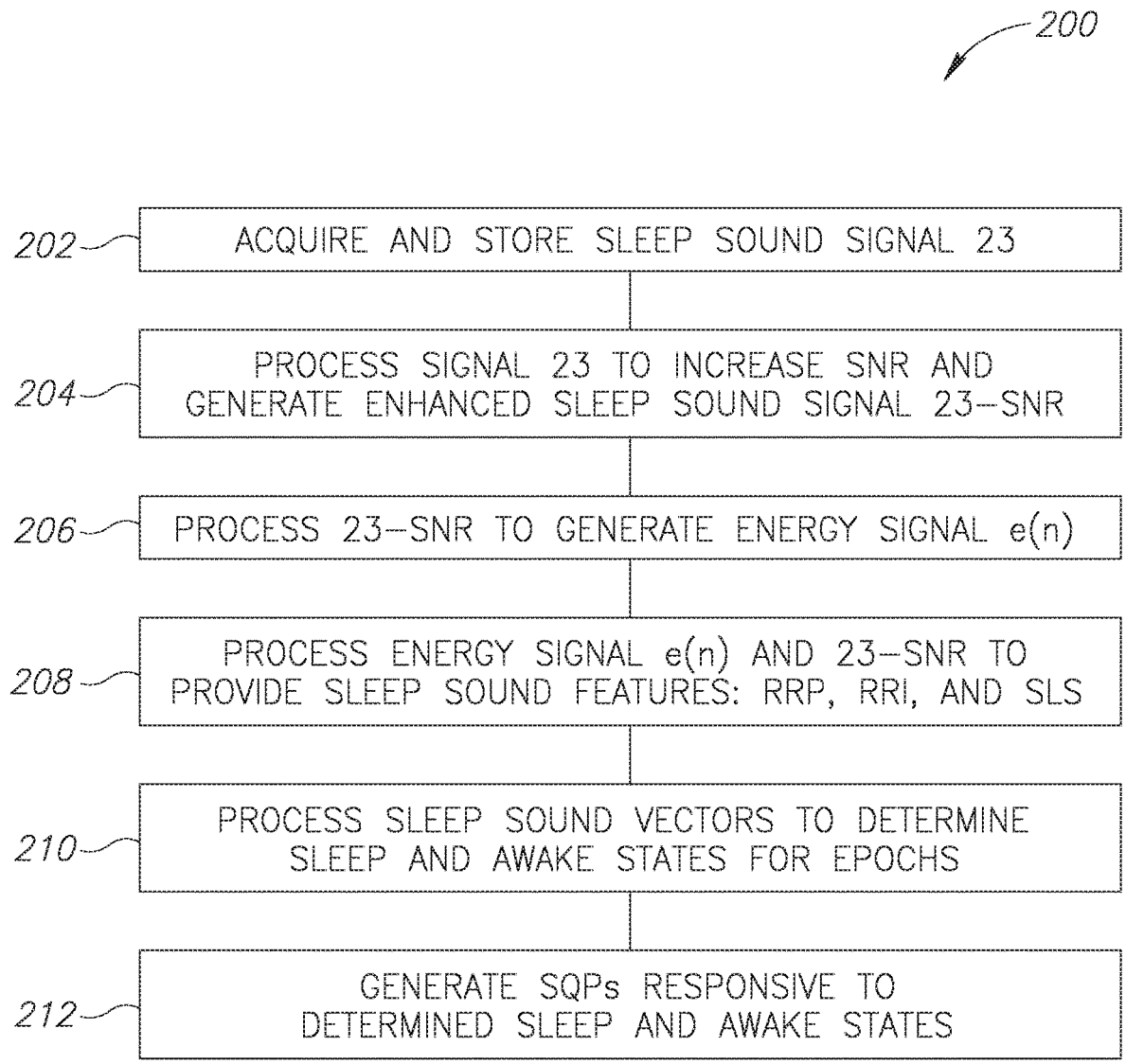
FIG. 2 shows a flow diagram that provides details of an algorithm by which the apparatus shown in FIG. 1 determines SQPs responsive to sleep sounds, in accordance with an embodiment of the invention.

Aspects of SleepDetective 20 and configuration and functioning of preprocessor 34, feature extractor 36, sleep period state classifier 38, and SQP generator 40, are discussed below with reference to a flow diagram 200 shown in FIG. 2.

In a block 202 SleepDetective 20 is turned on and microphone 22 registers sounds made in or reaching room 102 and transmits, optionally analog, electronic signals that form sleep sound signal 23 to computer system 30. The computer system may convert sleep sound signal 23 from an analog signal to a digital signal and optionally stores the digital sleep sound signal in memory 32. Hereinafter, unless otherwise specified, reference to sleep sound signal 23 is assumed to reference the digital form of the sleep sound signal. Sleep sound signal 23 includes background sounds, such as background sounds noted above, and respiratory sounds made by person 100 during a sleep period. The sleep sound signal may include electromagnetic interference from power lines and appliances in a neighborhood of SleepDetective 20. A sleep period, for which an associated sleep sound signal 23 is acquired, may have different durations, and may of course have duration of a nominal full night's sleep of 6-8 hours.

In a block 204, preprocessor 34 processes signal 23 stored in memory 32 to increase signal to noise ratio (SNR) of signal 23 and reduce vitiation of breathing and snore sounds by noise to provide a SNR enhanced signal 23-SNR. Optionally, preprocessor 34 employs a noise reduction algorithm that operates to reduce noise due to stationary processes and emphasize non-stationary events such as snores and inhale breaths to generate signal 23-SNR. In an embodiment of the invention, an algorithm based on a Wiener-filter and a decision-directed approach such as proposed by Scalart P, Filho J V (1996); "Speech Enhancement Based on A Priori Signal to Noise Estimation"; Conf Proc IEEE International Conference on Acoustics, Speech, and Signal Processing 2: 629-632.

In a block 206 feature extractor 36 optionally processes signal 23-SNR to segment the signal into a sequence of time segments and generate an energy signal e(n) for each segment, where n refers to a sequential integer index labeling the segments. In an embodiment of the invention, the energy signal e(n) for a given n-th segment is equal or proportional to a sum of squared amplitudes of signal 23-SNR in the segment, or an average of the squared amplitudes in the segment, weighted by a suitable window function. Optionally, the segments are 60 ms (milliseconds) long with an overlap of about 75% providing an energy value at 15 ms time intervals of the energy signal e(n), and the window function is a Gaussian window function. In an embodiment of the invention, the energy values are provided and stored in memory 32 in units of dB (decibels).

In a block 208 feature extractor 36 processes the energy signal e(n) and/or signal 23-SNR to determine values of sleep sound features for a sleep period vector that may be used to distinguish sleep states from awake states. In an embodiment, the sleep sound features comprise a respiratory rhythm period, RRP, a respiratory rhythm intensity, RRI, and a snore likelihood score (SLS) for the given period of time.

To determine a RRP, feature extractor 36 segments the energy signal e(n) into a sequence of time segments and for each time segment processes the energy signal e(n) in the segment optionally to determine an autocorrelation function $R(\tau)$ for the segment as a function of time displacement $\tau$. Autocorrelation function $R(\tau)$ is used to determine periodicity of the sleep sounds for the segment and a RRP for person 100 during the segment. In an embodiment of the invention, RRP is determined to be equal to a value at a time displacement $\tau=\tau_1$ for which $R(\tau)$ reaches a first maximum after a maximum of the autocorrelation function at $\tau=0$. It is noted that whereas extractor 36 is described as determining RRP using an autocorrelation function, an embodiment of the invention is not limited to autocorrelating e(n) to determine RRP, and any of various other methods such as a fast Fourier transform (FFT) may be used to determine RRP.

Figure 3A:
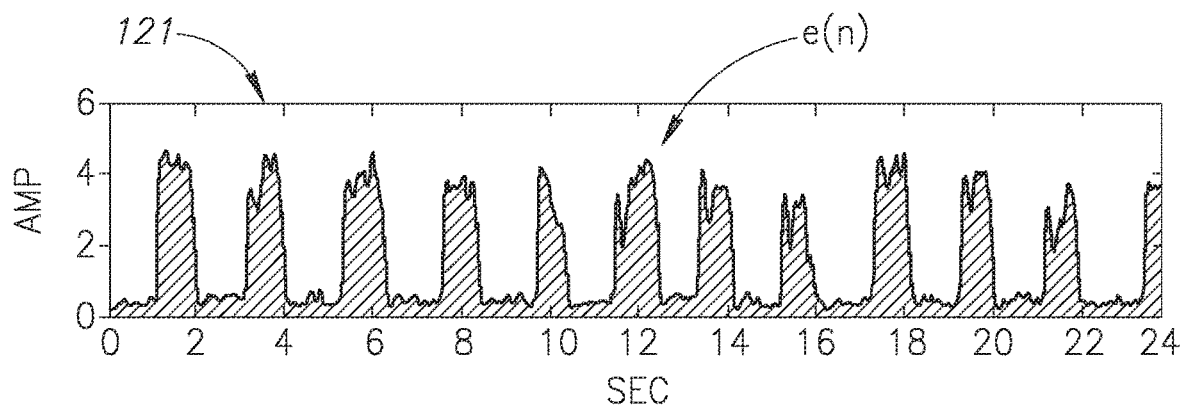
FIG. 3A shows a graph of sleep sounds made by the person shown in FIG. 1, in accordance with an embodiment of the invention.
Figure 3B:
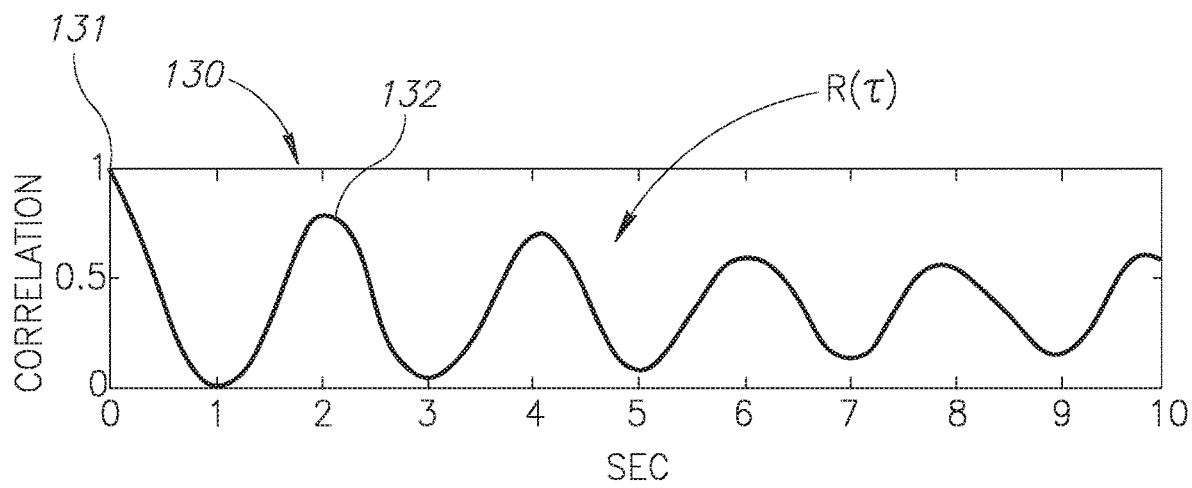
FIG. 3B shows a graph of an autocorrelation function of the sleep sounds shown in FIG. 3A that may be used to determine a RRP for the sleep sounds shown in FIG. 2A, in accordance with an embodiment of the invention.

By way of numerical example, in an embodiment of the invention, feature extractor 36 segments energy signal e(n) into 24 s (second) time segments overlapping by 19 seconds and $\tau_1$ is a time displacement $\tau$ between 1 sec and 10 sec at which $R(\tau)$ peaks. FIG. 3A shows a graph 120 of function e(n) as a function of time acquired for person 100 by SleepDetective 20. The abscissa is in units of seconds and the ordinate, which indicates amplitude of e(n) in arbitrary units. FIG. 3B shows a graph 130 of function $R(\tau)$ as a function of time displacement $\tau$. $R(\tau)$ exhibits a first peak 132 at a time displacement $\tau_1=2$ sec following a peak 131 of $R(\tau)$ at $\tau=0$, indicating that person 100 is breathing at about 30 breaths per minute. It is noted that energy functions e(n) and autocorrelation function shown in FIGS. 3A-3B were acquired for a real person using a SleepDetective similar to SleepDetective 20.

Figure 3C:
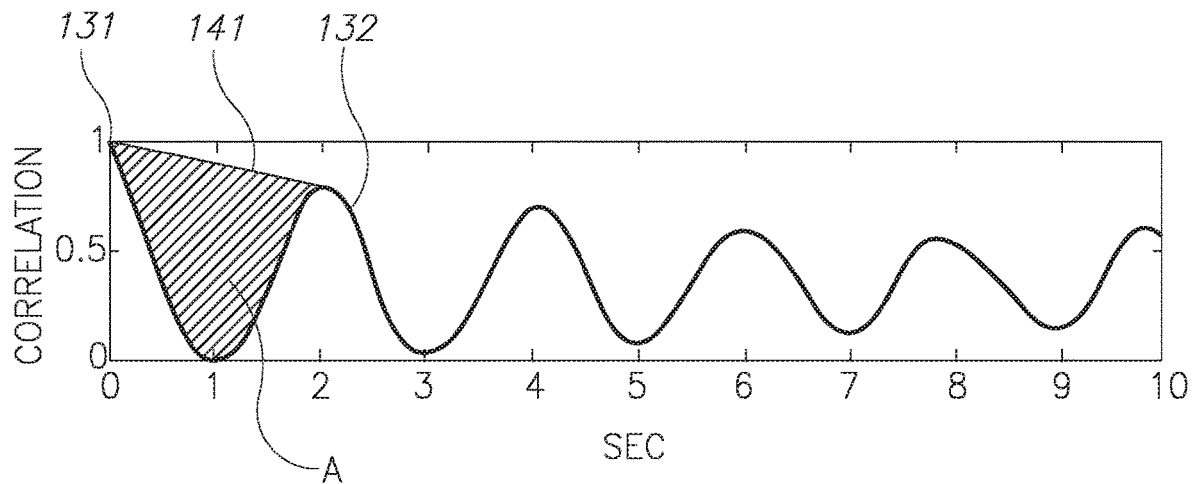
FIG. 3C illustrates features of the autocorrelation function shown in FIG. 3B that are used to determine a RRI for the RRP, in accordance with an embodiment of the invention.

In an embodiment of the invention, RRI is determined to be equal to a value of $R(\tau_1)$ times an area factor "AF", in symbols RRI=$R(\tau_1)$AF. Area factor AF may be determined responsive to an area A between peaks 131 and 132 of $R(\tau)$ at $-\tau=0$ and $\tau_1$ respectively and a straight line tangent to the peaks. FIG. 3C shows a graph 140 of $R(\tau)$ and a line 141 having slope "a" as a function of $\tau$ that is tangent to peaks 121 and 122. The area A responsive to which AF may be determined is shown shaded. In an embodiment of the invention, area factor AF is determined in accordance with an expression $$AF = \frac{1}{\tau_{peak}} \sum_{\tau=0}^{\tau_1} (a\tau + 1 - R(\tau))^2.$$

To an extent that RRI is larger, the RRP with which it is associated is a more dominant characteristic of the time dependence of the energy function e(n), and e(n) is closer to resembling a harmonic function with frequency 1/RRP.

Feature extractor 36 generates a snore likelihood score SLS as a measure of snore likelihood. To generate the SLS, feature extractor 36 optionally processes each time segment into which energy signal e(n) is segmented and corresponding time segment of signal 23-SNR to determine if the time segment of e(n) (and corresponding time segment of 23-SNR) contains an audio event that is a candidate for identity as a snoring sound or snore. Hereinafter reference to the time segment of e(n) may be considered to include reference to the corresponding time segment of 23-SNR. Any of various snore detection algorithms may be used to determine if a given time segment of energy signal e(n) exhibits an audio event that may be a candidate for being a snoring sound. Optionally, the time segments used to identify snore candidate audio events have a same duration as the time segments used to determine RRP and RRI.

In an embodiment of the invention, feature extractor 36 identifies a portion of a time segment of energy signal e(n) as a snore candidate audio event, if the portion exhibits energy greater than a suitable threshold energy $E_{th}$ and has a duration, $\tau_d$, greater than a suitable minimum duration $\tau_{dmin}$. For each snore candidate audio event, feature extractor 36 processes e(n) and/or 23-SNR to generate a snore feature set (optionally referred to as a snore feature vector) that may be used to determine whether to classify the audio event as a snore. Optionally, feature extractor 36 uses a snore model, represented by $\lambda_S$ to determine a probability that a snore candidate audio event is a snore, and a noise model, represented by $\lambda_N$ to determine a probability that a snore candidate audio event is noise. If $x_i$ represents a snore feature vector for an i-th snore candidate audio event that occurs at a time $t_i$, a probability that the event is a snore may be written $p(x_i|\lambda_S)$ and the probability that the event is noise may be written $p(x_i|\lambda_N)$.

In an embodiment of the invention, feature extractor 36, determines a value for SLS for each of a sequence of snore detection time segments of e(n) having duration, $\tau_{SLS}$, and segment overlap $(\tau_{SLS}-\Delta\tau_{SLS})$ Feature extractor 36 therefore provides value of SLS for energy signal e(n) at $\Delta\tau_{SLS}$ time intervals, that is, a resolution of $\Delta\tau_{SLS}$ seconds.

In an embodiment of the invention, feature extractor 36 determines an event score, $s(x_i)$, responsive to $p(x_i|\lambda_S)$ and $p(x_i|\lambda_N)$ for a snore candidate audio event, and a value for SLS responsive to $s(x_i)$. Optionally, the event score $s(x_i)$ is a function of a ratio of $p(x_i|\lambda_S)/p(x_i|\lambda_N)$. In an embodiment $s(x_i)$ is determined in accordance with an expression, $$s(x_i) = \log p(x_i|\lambda_S) - \log p(x_i|\lambda_N)$$

and a value for SLS for a given snore detection time segment is determined equal to a maximum of event scores $s(x_i)$ for snore candidate audio events that occur at corresponding times q during the snore detection time segment. In symbols, $$SLS = \max\{s(x_i) : t_i \in \tau SLS\}.$$

In an embodiment of the invention, $\lambda_S$ and $\lambda_N$ may be a Gaussian mixture models or an Adaboost classifier, $\tau_{SLS}$ has duration of 60 seconds and $\Delta\tau_{SLS}$ a duration of 5 seconds.

In a block 210 sleep state classifier 38 uses sleep sound features RRP, RRI and SLS determined by feature extractor 36 to determine sleep states for each of a sequence of time segments of duration $T_S$, hereinafter also referred to for convenience as "epochs", during person 100's nighttime sleep. Optionally, the first epoch of the sequence occurs at a time $t_o$ substantially at a time at which person 100 lies down to go to sleep and a last epoch in the sequence occurs at a time $t_J$ substantially at a time at which the person awakes and rises from sleep. If any of sleep sound features RRP, RRI and SLS were determined by feature extractor 36 for time periods having duration different from $T_S$, sleep state classifier 38 averages or otherwise appropriately processes the sleep sound features to provide sleep sound features that correspond to the durations of the epochs.

Let a sleep sound feature vector having values for RRP, RRI and SLS for a given epoch in the sequence at a time t be referred to as an "epoch feature vector" and be represented by $X_E(t)$. Let a sleep period state which person 100 experiences during an epoch at time t be represented by $ST(t)$ and be referred to as an epoch state. In an embodiment of the invention, sleep state classifier 38 processes epoch feature vectors $X_E(t_o), X_E(t_1) \ldots X_E(t_J)$ for the sequence of epochs at times $t_j$, $0 \leq j \leq J$, of the nighttime sleep period of person 100 using an optionally second order GMM and an optionally two state HMM to determine whether an epoch state "$ST(t_j)$" for an epoch at time $t_j$ is a sleep state "S" or an awake state "A".

For a given epoch feature vector $X_E$, the GMM provides a probability that $X_E$ is generated by a sleep state "S" or an awake state "A". If the parameters, that define the GMM are represented by $\hat{\lambda}$, the probability of a given $X_E$ being generated by a sleep state S may be written $p(X_E|\hat{\lambda}, S)$, and the probability that $X_E$ is generated by an awake state A is given by $p(X_E|\hat{\lambda}, A)$. The GMM parameters represented by $\hat{\lambda}$ include an average $\mu$ and standard deviation $\sigma$ for each of the components RRP, RRI and SLS of the vectors $X_E$ and a correlation matrix $\Sigma$ for the components.

The HMM provides a transition matrix that provides a probability that a sleep state S or awake state A for an epoch at time $t_j$, remains the same for the next epoch at time $t_{j+1}$ or transitions to an awake state A or a sleep state S respectively. If the transition matrix for the two state HMM is represented by "TM", the transition probabilities may be represented by $T(S \rightarrow S)$, $T(A \rightarrow A)$, $T(S \rightarrow A)$, and $T(A \rightarrow S)$, where the arguments indicate the transitions to which the probabilities refer.

The parameters GMM represented by $\hat{\lambda}$ and the transition probabilities in the HMM matrix are determined in a training procedure using a training set of epochs for which sleep and awake states have been determined using an appropriate gold standard such a PSG and optionally human observation and discrimination.

In terms of the GMM and HMM, a probability of person 100 being in an epoch state $ST(t_j)$ for an epoch at time $t_j$ and SleepDetective 20 registering an epoch vector $X_S(t_j)$ if person 100 is in an epoch state $ST(t_{j-1})$ at time $t_{j-1}$ may be given by an expression, $$p(X_S(t_j)|\hat{\lambda}, ST(t_j)) T(ST(t_{j-1}) \rightarrow ST(t_j)).$$

Given the sequence of J+1 epoch feature vectors $X_E(t_o)$, $X_E(t_1) \ldots X_E(t_J)$ determined by SleepDetective 20 for person 100, a probability P(J) that the sequence was generated by a corresponding sequence of epoch states $ST(t_o)$, $ST(t_1) \ldots ST(t_J)$ may be expressed as, $$P(J) = p_o \Pi_1^J p(X_S(t_j)|\hat{\lambda}, ST(t_j)) T(ST(t_{j-1}) \rightarrow ST(t_j)),$$

where the probability $p_o = p(X_S(t_o)|\hat{\lambda}, ST(t_o))$ of a first state in the sequence is considered to have a known value.

In an embodiment of the invention, sleep state classifier 38 determines a sequence, hereinafter referred to as a "most probable sequence (MPS)" of epoch states $ST(t_o)^*$, $ST(t_1)^* \ldots ST(t_J)^*$ that maximizes P(J), optionally using a Viterbi algorithm. Sleep state classifier 38 may use the MPS and a probability that the MPS determines for an epoch state being a sleep state or an awake state to calculate a sleep state classification metric (CM) for the epoch that is advantageous in discriminating sleep states from awake states. If $p(t_j,A)$ is a probability provided by the MPS that person 100 is in an awake state during the epoch at a time $t_j$ and $p(t_j,S)$ is a probability that the person is in a sleep state, the classification metric $CM(t_j)$ be determined by an expression, $$CM(t_j)=\alpha \log [p(t_j,A)/p(t_j,S)],$$

where $\alpha$ is a normalizing constant and log may be the natural logarithm, that is the logarithm to the base e. In an embodiment, sleep period state classifier 38 determines whether person 100 is in an awake state if $CM(t_j)$ is less than a classifier threshold, CT, and in a sleep state if $CM(t_j)$ is greater than the CT threshold.

Figure 4A:
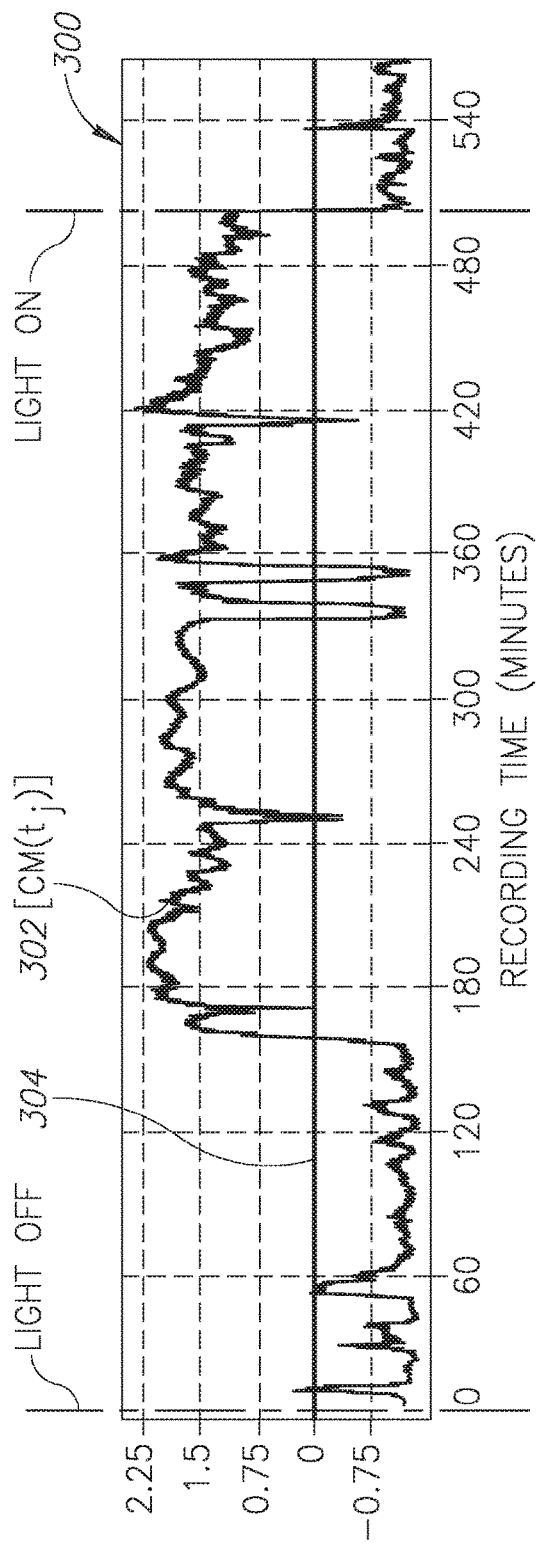
FIG. 4A shows a graph of a classification metric generated responsive to sleep sound feature vectors that may be used to distinguish sleep and awake states in a sleep period of the person shown in FIG. 1, in accordance with an embodiment of the invention.

FIG. 4A shows a graph 300 showing a $CM(t_j)$ curve 302 determined in accordance with an embodiment of the invention, for the nighttime sleep period of person 100 from a time of lights out when the person lay down to sleep to a time about eight and a half hours later at lights on when the person awoke and rose from sleep. The abscissa of the graph is graduated in minutes, the ordinate is graduated in arbitrary units and a CT threshold 304 is shown equal to 0. SleepDetective 20 determines that person 100 is in a sleep state when the $CM(t_j)$ curve 302 is greater than CT threshold 304.

Figure 4B:
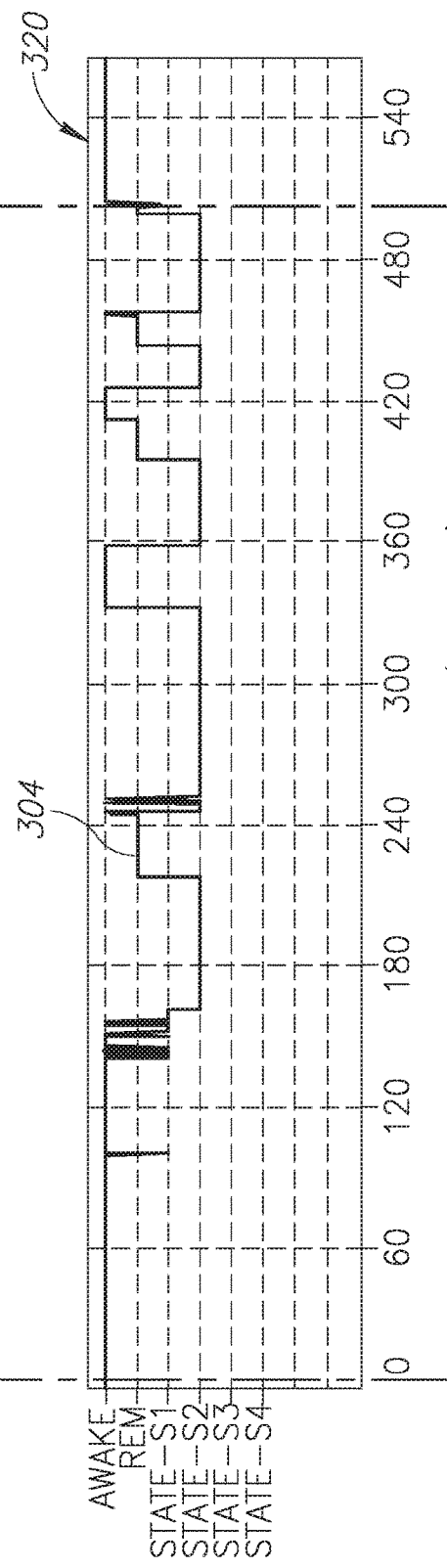
FIG. 4B shows a graph of sleep and awake states determined for the sleep period of the person shown in FIG. 1 using a PSG apparatus.

Data used to provide graph 300 and the $CM(t_j)$ curve 302 shown in the graph was acquired in an experiment conducted with a real person by a SleepDetective in accordance with an embodiment of the invention similar to SleepDetective 20 during a nighttime sleep period of the person. The data for graph 300 was acquired simultaneously with control data acquired using PSG apparatus. The control data was used to distinguish awake states and various sleep states of the person during the nighttime sleep period. Among the sleep states distinguished by the control data are REM sleep and NREM sleep states S1, S2, S3 and S4. FIG. 4B shows a graph 320 having a sleep period state curve 322 which indicates the various sleep and awake states distinguished by the PSG apparatus for the person's nighttime sleep period.

Analysis of the data and curves shown in graphs 300 and 320, and similar data acquired for sleep periods of other people indicate that a SleepDetective similar to SleepDetective 20 distinguishes sleep states and awake states with about 82% accuracy.

In a block 212 of algorithm 200 sleep and awake states determined by sleep period state classifier 38 responsive to the classification metric $CM(t_j)$ and classification threshold CT are used by SQP generator 40 to calculate values for at least one of various SQPs that may be used to indicate quality of sleep for person 100. By way of example, an SQP that may be used to indicate a person's quality of may be: total sleep time (TST)—a sum of the durations of sleep states in a sleep period; sleep latency (SL)—an elapsed time to falling asleep from a time of lying down to go to sleep; sleep efficiency (SE)—a ratio between TST and total time spent lying down to sleep during the sleep period; wake-time after sleep onset (WASO)—a sum of the durations of awake states during the sleep period; and an awakening index (AI)—equal to an average number of times per hour a person awakes from sleep during the sleep period.

The following SleepDetective SQP table shows values and standard deviations for the SQPs listed above that were acquired for sleep periods of 95 people by a PSG apparatus and a SleepDetective in accordance with an embodiment of the invention similar to SleepDetective 20.

| SleepDetective SQP | | |
|---|---|---|
| SQP | PSG | SleepDetective |
| SL (min) | 64.3 ± 69.0 | 54.8 ± 59.2 |
| SE (%) | 65 ± 13 | 69 ± 16 |
| TST (min) | 290 ± 58 | 309 ± 68 |
| WASO (min) | 43 ± 31 | 52 ± 54 |
| AI (e/hr) | 4.7 ± 3.3 | 5.3 ± 5.1 |

The SleepDetective SQP table shows that values for SPQs acquired by the SleepDetective in accordance with an embodiment of the invention and the PSG apparatus are in substantial agreement and are well within standard deviations of each other.

Whereas in the above example, an HMM model was configured having only two sleep period states, an awake state and a sleep state, an embodiment of the invention is not limited to distinguishing two states one of which is a sleep state. For example, in an embodiment of the invention, sleep period feature vectors in accordance with an embodiment of the invention may be used to distinguish REM sleep states and NREM sleep states as well as awake states. Optionally, the sleep vectors used to distinguish REM and NREM sleep states include at least one feature, a "lability feature", that that provides a measure of lability of activity of a person during a sleep period. The at least one feature may comprise a feature or any combination of features chosen from the group of features comprising a measure of respiration rate variability (RRV), variability of time delay (VOD) between a breath inhale and a breath exhale, variability in RRI, and snores duration.

Figure 5:
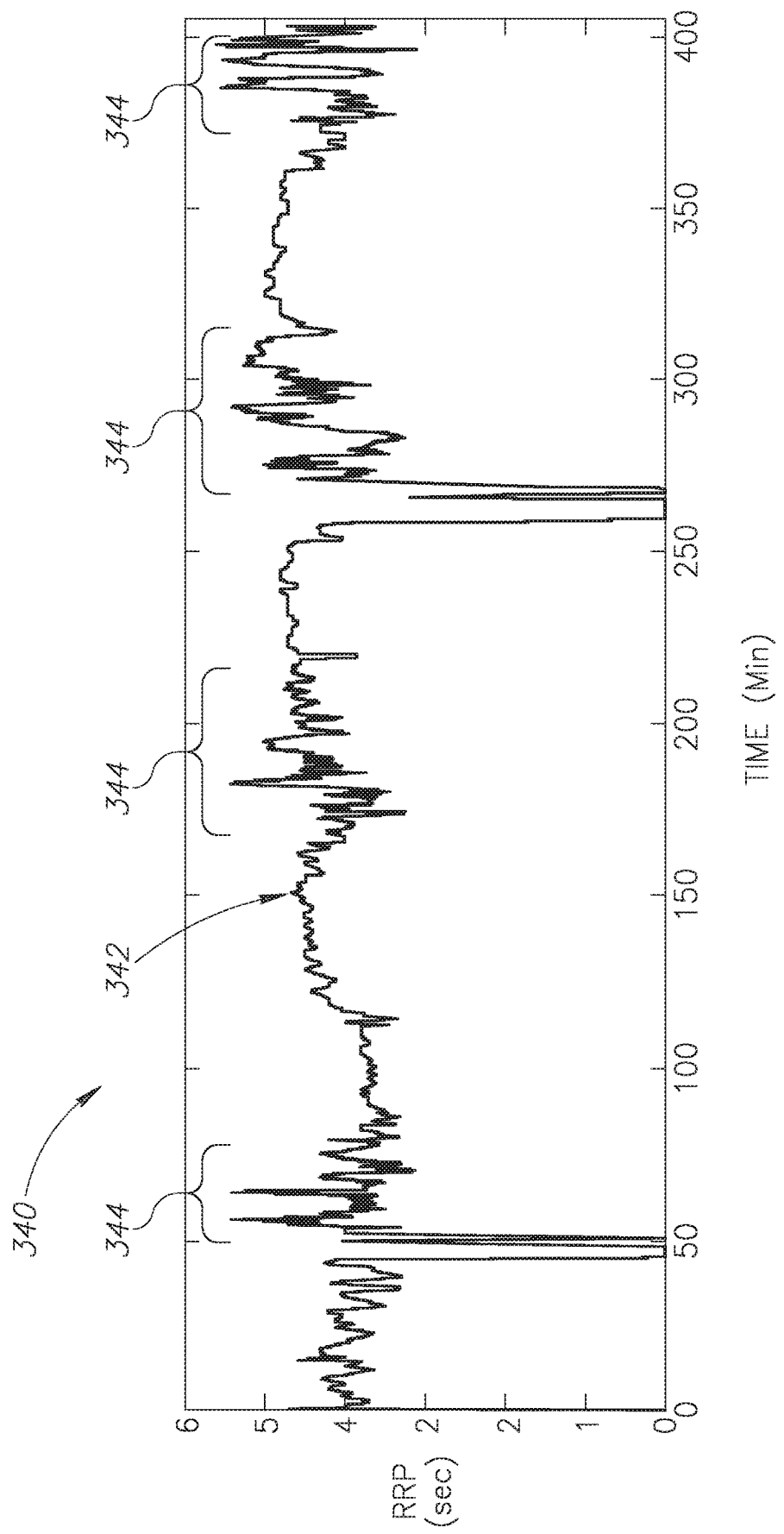
FIG. 5 shows a graph of RRP that shows correlation between REM sleep states and elevated respiration rate variability RRV, in accordance with an embodiment of the invention.

FIG. 5 shows a graph 340 that indicates how RRV in accordance with an embodiment of the invention may be used to indicate a REM sleep state. Graph 340 shows a curve 342 of RRP acquired for a woman during a nighttime sleep period by a SleepDetective in accordance with an embodiment of the invention similar to SleepDetective 20. REM states during the nighttime sleep period were determined using a PSG apparatus and are indicated by brackets 344. The graph indicates that the REM sleep states 344 identified by the PSG apparatus substantially coincide with periods of elevated respiration rate variability RRV.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A contactless method for determining levels of one or more sleep disorder factors, the method comprising:
    using a non-contact microphone, acquiring a real-time sleep sound signal representing sounds made by a person during sleep, and conveying the signal to a processor;
    segmenting by the processor the sleep sound signals into a plurality of epochs;
    generating by the processor at least one sleep sound feature vector for each of the epochs in the plurality of epochs, wherein for each of the epochs, the generation of the at least one sleep sound feature vector for the respective epoch includes determining an autocorrelation function $R\tau$ as a function of time displacement $\tau$ of sleep sounds that occurred during the respective epoch, and specifying that the at least one sleep sound feature vector for the respective epoch is equal to a value at a time displacemen $\tau=\tau_1$ for which the autocorrelation function reaches a first maximum after a maximum of the autocorrelation function at $\tau=0$;
    for each of the epochs in the plurality of epochs, determining by the processor a set of first probabilities using a first model and based on the at least one sleep sound feature vector generated for the respective epoch, said set of first probabilities indicating probabilities as to whether the respective epoch is associated with respective sleep period states from a plurality of predefined sleep period states;
    associating each epoch in the plurality of epochs with one of the sleep period states from the plurality of predefined sleep period states based on the set of first probabilities;
    determining by the processor a second probability for each set of two adjacent epochs in the plurality of epochs, the second probability indicating a probability of transitioning from the sleep period state associated with the preceding epoch in the respective set to the sleep period state associated with the succeeding epoch in the respective set;
    wherein the processor is configured to determine the sleep period state of each of the epochs in the plurality of epochs based on the set of first probabilities and the second probability, wherein the sleep period state of each of the epochs in the plurality of epochs is determined during the respective epoch; and
    utilizing said determined sleep period states, determining levels of sleep disorder factors selected from:
        total sleep time (TST)—a sum of the durations of sleep states in a sleep period;
        sleep latency (SL)—an elapsed time to falling asleep from a time of lying down to go to sleep;
        sleep efficiency (SE)—a ratio between TST and total time spent lying down to sleep during the sleep period;
        wake-time after sleep onset (WASO)—a sum of the durations of awake states during the sleep period; and
        an awakening index (AI)—equal to an average number of times per hour a person awakes from sleep during the sleep period;
    wherein the first model comprises a Gaussian mixture model (GMM), and the second probability for each set of two adjacent epochs in the plurality of epochs is determined using a second model, and the second model comprises a hidden Markov model (HMM).

2. The method according to claim 1, wherein the set of first probabilities includes a probability that the person is experiencing an awake state p(A) during the respective epoch and a probability p(S) that the person is experiencing a sleep state during the respective epoch.

3. The method according to claim 2, further comprising, for each epoch, determining a value for a classification metric, CM, based on p(A) and p(S) for the respective epoch.

4. The method according to claim 3, further comprising, for each epoch, determining that the person is experiencing an awake state or a sleep state during the respective epoch based on the respective value of the CM and a classifier threshold for the CM value.

5. The method according to claim 1, further comprising determining a sleep quality parameter (SQP) indicative of a quality of sleep for the person based on the determined sleep period state of the epochs.

6. The method according to claim 5, wherein the determination of the SQP comprises determining a value for each of a total sleep time (TST); sleep latency (SL); sleep efficiency (SE); wake-time after sleep onset (WASO); and/or an awakening index (AI).

7. The method according to claim 1, wherein the at least one sleep sound feature vector further comprises a value for a respiration rate intensity (RRI); a snore likelihood; and/or at least one lability feature.

8. The method according to claim 7, wherein a value for RRI is determined by determining a line tangent to a maximum of the autocorrelation function for a time displacement equal to zero and a first maximum of the autocorrelation function for a time displacement greater than zero.

9. The method according to claim 8, further comprising determining a value for an area factor based on an area between the tangent line and the autocorrelation function, and determining the value for RRI based on the area function and the magnitude of the first maximum.

10. The method according to claim 7, wherein a lability feature comprises a measure of respiration rate variability (RRV), variability of time delay (VOD) between a breath inhale and a breath exhale, variability in RRI, and/or snores duration.

11. The method according to claim 1, further comprising:
    for at least one of the epochs in the plurality of epochs,
        identifying a portion of the sleep sound signal having an energy greater than a threshold energy and duration greater than a minimum duration;
        determining a snore feature vector for the portion;
        determining a probability, p(snore), that the portion exhibits a snore and a probability, p(noise), that the portion exhibits noise rather than a snore based on the snore feature vector;
        determining a snore likelihood for the sound feature vector of the at least one epoch based on p(snore) and p(noise).

12. The method according to claim 11, wherein determining the snore likelihood comprises determining the snore likelihood to be equal to a snore likelihood score (SLS) that is a function of p(snore) and p(noise).

13. The method according to claim 12, further comprising determining the SLS, wherein determining SLS includes determining an event score equal to (log p(snore)−log p(noise) for the portion.

14. The method according to claim 13, wherein determining the SLS comprises determining SLS to be equal to a maximum of event scores for portions of the sleep sound signal in the epoch.

15. Apparatus for determining levels of one or more sleep disorder factors, the apparatus comprising:
- at least one non-contact microphone configured to acquire, in real-time, a sleep sound signal representing sounds made by a person during sleep; and
- a processor having an executable instruction set configured to: segment the sleep sound signals into a plurality of epochs;
- generate at least one sleep sound feature vector for each epoch in the plurality of epochs, wherein for each of the epochs, the generating of the at least one sleep sound feature vector for the respective epoch includes determining an autocorrelation function $R\tau$ as a function of time displacement $\tau$ of sleep sounds that occurred during the respective epoch and specifying that the at least one sleep sound feature vector for the respective epoch is equal to a value at a time displacement $\tau=\tau_1$ for which the autocorrelation function reaches a first maximum after a maximum of the autocorrelation function at $\tau=0$;
- for each of the epochs in the plurality of epochs, determine a set of first probabilities using a first model and based on the at least one sleep sound feature vector generated for the respective epoch, the set of first probabilities indicating probabilities as to whether the respective epoch is associated with respective sleep period states from a plurality of predefined sleep period states;
- associate each epoch in the plurality of epochs with one of the sleep period states from the plurality of predefined sleep period states based on the set of first probabilities;
- determine a second probability for each set of two adjacent epochs in the plurality of epochs, the second probability indicating a probability of transitioning from the sleep period state associated with the preceding epoch in the respective set to the sleep period state associated with the succeeding epoch in the respective set;
- determine the sleep period state of each of the epochs in the plurality of epochs based on the set of first probabilities and the second probability, wherein the sleep period state of each of the epochs in the plurality of epochs is determined during the respective epoch; and
- utilize said determined sleep period states, determining levels of sleep disorder factors selected from:
  - total sleep time (TST)—a sum of the durations of sleep states in a sleep period;
  - sleep latency (SL)—an elapsed time to falling asleep from a time of lying down to go to sleep;
  - sleep efficiency (SE)—a ratio between TST and total time spent lying down to sleep during the sleep period;
  - wake-time after sleep onset (WASO)—a sum of the durations of awake states during the sleep period; and
  - an awakening index (AI)—equal to an average number of times per hour a person awakes from sleep during the sleep period;
- wherein the first model comprises a Gaussian mixture model (GMM), and the second probability for each set of two adjacent epochs in the plurality of epochs is determined using a second model, and the second model comprises a hidden Markov model (HMM).

16. Apparatus according to claim 15, wherein the at least one non-contact microphone comprises a plurality of non-contact microphones.

17. Apparatus according to claim 15, wherein at least a portion of the apparatus is housed in a smartphone, PC, laptop, and/or a work book.

18. Apparatus according to claim 15, wherein the processor is further configured to:
- for at least one epoch identify a portion of the sleep sound signal having an energy greater than a threshold energy and duration greater than a minimum duration;
- determining a snore feature vector for the portion;
- determine a probability, p(snore), that the portion exhibits a snore and a probability, p(noise), that the portion exhibits noise rather than a snore based on the snore feature vector;
- determine a snore likelihood for the sound feature vector of the at least one epoch based on p(snore) and p(noise).

* * * * *